(12) United States Patent
Malczewski

(10) Patent No.: US 6,473,175 B1
(45) Date of Patent: Oct. 29, 2002

(54) METHOD FOR ANALYZING IMPURITIES IN A GAS STREAM

(75) Inventor: Mark Leonard Malczewski, N. Tonawanda, NY (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 09/552,734

(22) Filed: Apr. 19, 2000

(51) Int. Cl.[7] .......................... G01N 21/62; G01N 1/00; G01N 1/22
(52) U.S. Cl. .......................................... 356/311; 356/36
(58) Field of Search .............................. 356/72, 36, 311, 356/313, 314, 315, 316

(56) References Cited

U.S. PATENT DOCUMENTS

| | | | |
|---|---|---|---|
| 3,032,654 A | 5/1962 | Fay et al. | 250/43.5 |
| 5,412,467 A | 5/1995 | Malczewski et al. | 356/316 |
| 5,473,162 A * | 12/1995 | Busch et al. | 356/311 |

OTHER PUBLICATIONS

"De–Oxo Manual", Valco Instruments Co. Inc., pp. 1–6 (1990).

* cited by examiner

Primary Examiner—F. L. Evans
(74) Attorney, Agent, or Firm—Donald T. Black

(57) ABSTRACT

A method of analyzing a sample gas for the presence of at least one gas impurity by combining a stream of sample gas with a stream of carrier gas to provide a combined stream of gas, directing the combined stream of gas through a column which preferentially removes the sample gas from the combined stream to produce a retentate stream of gas, and analyzing the retentate stream of gas for the presence of the at least one gas impurity.

27 Claims, 3 Drawing Sheets

METHOD FOR ANALYZING IMPURITIES IN A GAS STREAM

BACKGROUND OF THE INVENTION

1. Field of the Invention

The invention relates to a method for analyzing a gas stream, for example, a hydrogen or oxygen gas stream, under continuous flow conditions to detect and quantify the concentration of one or more gaseous contaminants.

2. Related Background Art

Ultra high purity supplies of process gases are essential in the manufacture of large scale integrated circuits. Measurement and control of impurities at the parts per billion (ppb) level are critical with the process gases utilized by semiconductor manufacturers in the production of integrated circuit devices. Semiconductor manufacturers utilize commercial purifiers to remove impurities from the process gases. Some of the more important impurities removed by these purifiers include oxygen, water, carbon monoxide, carbon dioxide, hydrogen, methane and nitrogen. Continuous monitoring of the process gas stream under continuous flow conditions is necessary to ensure that the gas stream maintains stringent purity requirements.

The gases of interest according to the present invention include, but are not limited to hydrogen, oxygen, nitrogen and air. Although not used in as great a volume as argon or nitrogen, hydrogen and oxygen are used in several key processing steps. Consequently, analysis of impurities in these gases is also important.

However, several sensitive analytical techniques for providing ppb limits of detection for various impurities cannot be applied to the impurity analysis of hydrogen and oxygen in gas streams under continuous flow conditions. These analytical techniques include emission spectroscopy and gas chromatography (GC) using a discharge ionization detector (DID). In addition, atmospheric pressure ionization mass spectrometers (APIMS) cannot be used to analyze impurities in oxygen gas. Additionally, these analytical techniques cannot analyze large volumes (generally flow rates greater than 10 cc/min) of sample gas streams under continuous flow conditions.

The DID detectors and the APIMS cannot be used for oxygen analysis because these techniques require that the sample gas have a higher ionization potential than that of the gaseous impurity to be determined. Common oxygen impurities have higher ionization potentials than oxygen.

Emission spectroscopy, on the other hand, cannot be used to analyze impurity levels in diatomic gases such as hydrogen, nitrogen and oxygen. Monoatomic gases such as argon, helium and the like readily transfer energy to lower ionization potential impurities which then can be detected. Diatomic gases have additional vibrational and rotational pathways to dissipate the energy from a plasma and hence do not transfer the energy to the impurities of interest. Consequently, the emission lines of the impurities cannot be detected in diatomic gases. Instead, only the spectrum of the sample is observed in most cases.

Previous attempts to solve this problem focused primarily on the use of GC-DID analyzers for hydrogen and oxygen sample gases and, more recently, on emission spectroscopy for detecting nitrogen in either hydrogen or oxygen gases.

With GC techniques, the typical carrier gas is purified helium. A small injection (e.g., 1–2 cc) of the sample gas (e.g., hydrogen) is made into the carrier gas stream. The 1–2 cc "slug" of sample gas is then moved to a device to handle the slug of sample gas. In the case of hydrogen sample gas, the device is typically a hot palladium membrane which selectively allows only the hydrogen gas to pass through it. The impurities are, therefore, retained in the helium carrier gas. A GC column is used to separate the impurities, and because they are contained in the helium carrier gas, a DID detector can be used for this analysis. GC techniques are, however, limited to batch analysis of the sample gas and do not allow analysis of a sample gas under continuous flow conditions.

Problems may arise when, for example, the oxygen gas sample must be consumed in a trap. The traps have a finite capacity for oxygen gas and are themselves consumed over time. Most commercial instruments currently available may accommodate only about 80–100 injections before they must be replaced, which may be equivalent to as little as one day of operation. To overcome this problem, dual traps may be employed with an automated regeneration sequence. While this approach minimizes the trap regeneration problem, it may add considerable expense and complexity to the process.

Newer trap materials with higher capacity for oxygen, may extend the number of injections possible between trap regenerations. Trap materials which exhibit reversible oxygen adsorption may eliminate the need for dual traps and separate high temperature regeneration steps involving hydrogen or carbon monoxide addition. Such a trap would receive an injection of oxygen sample containing the impurities of interest. The trap material would hold up the oxygen while allowing the impurities to pass through. Before the oxygen breaks through the trap material, and affects the detector's response, carrier gas is flowed in the reverse direction to sweep the oxygen off the trap to vent. This process continues while the impurities separate on the analytical column and are quantified by the DID detector. If all of the oxygen can be purged off the trap material in the time required to analyze the sample the process can be repeated indefinitely and only a single trap is required. While this modification represents an improvement to the GC-DID analysis of UHP oxygen samples it still is a batch or discrete analysis.

It would be highly desirable to provide a continuous, simple and reliable method for analyzing one or more impurities in a gas stream under continuous flow conditions while minimizing the difficulties associated with the systems previously described.

SUMMARY OF THE INVENTION

The present invention provides a method for analyzing a sample gas for the presence of at least one gas impurity. The method comprises the steps of: (a) combining a stream of a sample gas with a stream of a carrier gas to generate a combined stream of gas; (b) directing the combined stream of gas through a column which preferentially removes the sample gas from the combined stream of gas to produce a retentate stream of gas; and (c) analyzing the retentate stream of gas by emission spectroscopy for the presence of at least one gas impurity.

In another aspect, the present invention provides a method for analyzing a sample gas for the presence of at least one gas impurity in the sample gas. The method comprises the steps of: (a) directing a stream of carrier gas through a column; (b) directing a stream of sample gas to the column which allows selective permeation of the at least one gas impurity from the stream of sample gas into the stream of carrier gas to produce a permeate stream of gas; and (c) analyzing the permeate stream of gas by emission spectroscopy for the presence of the at least one gas impurity.

This brief summary has been provided so that the nature of the invention may be understood quickly. A more complete understanding of the invention can be obtained by reference to the following detailed description of the preferred embodiments thereof in connection with the attached drawings.

DETAILED DESCRIPTION OF THE INVENTION

Figure 1:
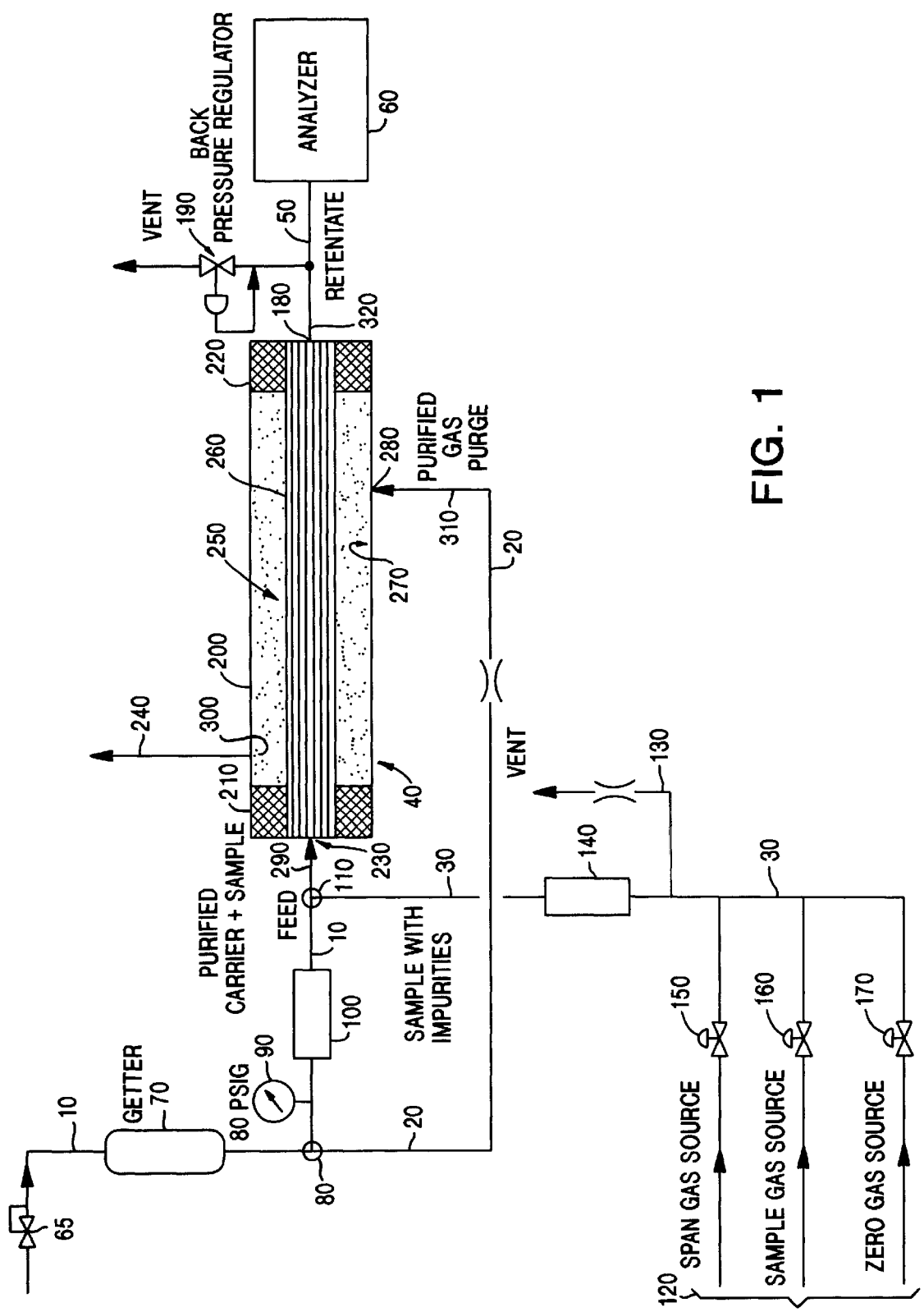
FIG. 1 is a schematic diagram of an impurity detection system of the present invention for analyzing gaseous impurities contained within a hydrogen gas stream.

The impurity detection system of FIG. 1 provides a system for detecting and quantifying gaseous impurities in a gas stream under continuous flow conditions. The sample gases of interest according to the present invention include, but are not limited to hydrogen, oxygen, nitrogen and air. The gas impurities of interest according to the present invention include, but are not limited to methane, water, carbon monoxide, carbon dioxide, nitrogen and oxygen. The impurity detection system comprises a carrier gas pathway 10, a carrier gas purge pathway 20, a sample gas pathway 30, an exchange column 40, a retentate pathway 50 and an analyzer 60.

The carrier gas pathway 10 comprises a source of carrier gas 65 in communication with a carrier gas getter 70, a carrier gas branch point 80, a carrier gas pressure gauge 90, a carrier gas flow control unit 100, a junction 110 and the carrier gas purge pathway 20. The carrier gas purge pathway 20 communicates between the carrier gas branch point 80 and the exchange column 40. In this embodiment, a mass flow controller is used as the carrier gas flow control unit 100. However, any means for regulating flow control may be used, such as a pressure regulator and/or a fixed orifice restriction.

The term "getter" refers to a device that is capable of selectively removing chemical impurities from a gas stream.

The sample gas pathway 30 comprises a valve manifold 120 in communication with a sample gas vent 130, a sample gas flow control unit 140 and the junction 110. The valve manifold 120 further comprises a span gas source 150, a sample gas source 160 and a zero gas source 170. In this embodiment, a mass flow controller is used as the sample gas flow control unit 140. However, any means for regulating flow control may be used, such as a pressure regulator and/or a fixed orifice restriction.

The retentate pathway 50 communicates between a retentate stream outlet port 180 of the exchange column 40 and the analyzer 60.

The exchange column 40 comprises a hollow tube 200 with a gas inlet end 210 and a gas outlet end 220, a feed stream inlet port 230, a purified carrier gas inlet port 280, the retentate stream outlet port 180, a permeate stream vent 240 and a membrane system 250, which generally comprises a semi-permeable membrane preferentially permeable to the sample gas 160. The materials of which the semi-permeable membrane 250 of the present invention is constructed include, but are not limited to polysulfone, ceramic and palladium.

The configuration of the membrane system 250 differs depending upon the source of the sample gas 160 under analysis. When the source of the sample gas 160 is hydrogen, the membrane system 250 comprises a series of hollow fibers 260 that are potted at both the gas inlet end 210 and the gas outlet end 220. An annular space 270 surrounds the series of hollow fibers 260 and is bounded by the inside of hollow tube 200, the gas inlet end 210 and the gas outlet end 220 of the hollow tube 200.

In one embodiment, the source of the carrier gas 65 is argon, and the source of the sample gas containing impurities 160 is hydrogen. A continuous stream of argon gas enters the carrier gas pathway 10 at a rate ranging from about 20 cc/min to about 200 cc/min and a pressure ranging from about 10 psig to about 150 psig, which is regulated by the carrier gas flow control unit 100. The continuous stream of argon gas passes through the getter 70 and reaches the branch point 80 where the argon gas not filling the carrier gas pathway 10 fills the carrier gas purge pathway 20, which supplies a continuous argon gas stream to the annular space 270 of the exchange column 40 via purified carrier gas inlet port 280. A continuous hydrogen gas sample containing impurities enters the sample gas pathway 30 at a rate ranging from about 20 cc/min to about 250 cc/min, which is regulated by the sample gas flow control unit 140. The carrier gas pathway 10 and the sample gas pathway 30 intersect at the junction 110 thereby causing the argon and hydrogen gas streams to combine and form a combined gas feed stream 290. The ratio of hydrogen sample gas to the argon carrier gas in the combined gas feed stream 290 ranges from about 4:1 to about 1:4 and preferably from about 2:1 to about 1:2 and more preferably is about 1:1.

The combined gas feed stream 290 enters the exchange column 40 at the feed stream inlet port 230 at a pressure ranging from about 50 psig to about 150 psig. A pressure difference between the series of hollow fibers 260 and the annular space 270 serves as the driving force moving hydrogen gas from the series of hollow fibers 260 into the annular space 270. The pressure difference ranges from about 70 psig to about 140 psig and preferably from about 80 psig to about 120 psig. Hydrogen gas diffuses from the series of hollow fibers 260 into the annular space 270 as the combined gas feed stream 290 passes through the exchange column 40. The diffused hydrogen gas and argon gas combine within the annular space 270 to form a permeate stream 300. If hydrogen gas is allowed to build up in the annular space 270, the diffusion rate of hydrogen gas rapidly will decrease. The carrier gas purge pathway 20 supplies purified argon gas in the form of a purge stream 310 to the annular space 270 within the exchange column 40 at a rate of about one 1/min. The purge stream 310 is introduced at atmospheric pressure into the annular space 270 at the purified carrier gas inlet port 280 of the exchange column 40. The purge stream 310 sweeps the diffused hydrogen gas located within the annular space 270 out of the exchange column 40 through the permeate stream vent 240. In this fashion, the hydrogen gas concentration within the annular space 270 is maintained near zero, thereby maximizing the hydrogen gas diffusion rate from the series of hollow fibers 260 into the annular space 270.

Gas flow exiting the exchange column 40 at the retentate stream outlet port 180 is referred to as a retentate stream 320.

The retentate stream 320 exits the exchange column 40 and enters the retentate pathway 50 at a flow rate ranging from about 50 cc/min to about 500 cc/min. A back-pressure regulator 190 is located along the retentate pathway 50 between the exchange column 40 and the analyzer 60.

In this embodiment, the analyzer 60 is an emission spectrometer. In another embodiment, the analyzer is an emission spectrometer such as that described in U.S. Pat. No. 3,032,654. In still another embodiment, the analyzer is an emission spectrometer as described in U.S. Pat. Nos. 5,412,467 and 5,831,728 the disclosures of which are incorporated herein by reference. In yet another embodiment, the analyzer 60 is an atmospheric pressure ionization mass spectrometer.

The retentate pathway 50 communicates with the exchange column 40 and the analyzer 60. The back-pressure regulator 190 is located within the retentate pathway 50 between the retentate stream outlet port 180 and the analyzer 60. The back-pressure regulator 190 functions to maintain proper pressure of the combined gas feed stream 290 as it enters the exchange column 40 and flows through the series of hollow fibers 260. The back-pressure regulator 190 also serves to maintain a constant pressure within the retentate pathway 50 which, in turn, allows constant inlet pressure to the analyzer 60, thereby stabilizing the response of the analyzer 60.

The retentate stream 320 contains the impurities of interest originally in the hydrogen sample gas now in the argon gas carrier which is suitable for introduction and analysis into the emission spectroscopic analyzer 60. Preferably, less than about 2% residual hydrogen gas remains within the retentate stream 320 as it flows to the analyzer 60.

If the impurity detection system were an ideal system, all of the hydrogen gas within the combined gas feed stream 290 would diffuse into the permeate stream 300 and none would remain in the retentate stream 320. Similarly, in the ideal system, none of the impurities within the combined gas feed stream 290 would diffuse into the permeate stream 300 and all the impurities would remain in the retentate stream 320. In this ideal case, the analyzer 60 could be calibrated using purified argon gas as the zero gas source 170 and spanned using a span gas source 150 containing known concentrations of the impurities of interest in an argon gas carrier.

Because the impurity detection system operates under non-ideal conditions, however, some hydrogen gas remains in the retentate stream 320 and each impurity diffuses to some extent into the permeate stream 300 and is lost to the analyzer 60. To compensate for this leaching, calibration of the analyzer 60 is performed under identical conditions as the analysis of the sample gas 160. Also, the zero gas source 170 must be hydrogen gas with all the impurities of interest removed, and the span gas source 150 must contain hydrogen gas as the balance gas.

For example, if the analyzer 60 is affected by residual hydrogen gas in the retentate stream 320, the effect would be demonstrated when the hydrogen zero gas 170 enters the carrier gas pathway 10. Consequently, an electronic adjustment could be made within the analyzer 60 to compensate for this during initial calibration of the analyzer 60. Similarly, if 20% of an impurity diffused into the permeate stream 300, 20% of the impurity would also diffuse when measuring the span gas source 150 and the gain in the analyzer 60 could be increased as compensation during span calibration of the analyzer 60. The analyzer 60 would continue to give an accurate impurity concentration as long as the percentage of hydrogen gas remaining in the retentate stream 320 remains constant, and the percentage of each impurity leaching to the permeate stream 300 also remains constant.

Figure 2:
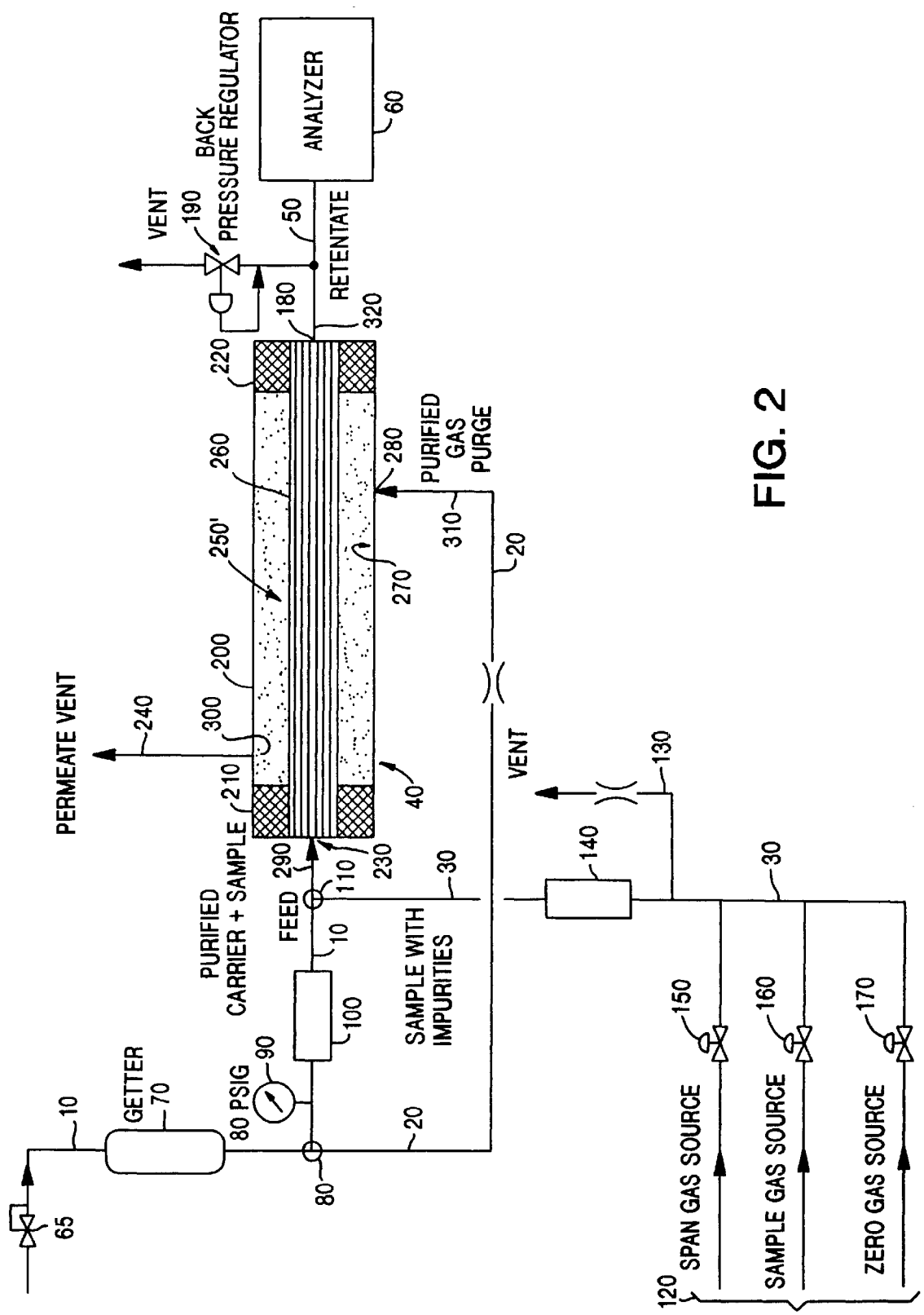
FIG. 2 is a schematic diagram of an impurity detection system of the present invention for analyzing gaseous impurities contained within an oxygen gas stream.

An alternate embodiment of the invention for analyzing a gas stream under continuous flow conditions to detect and quantify the concentration of one or more pre-selected gaseous contaminants is illustrated in FIG. 2. In this alternate embodiment, the configuration of the impurity detection system is basically similar to that of FIG. 1 with like reference numerals used to identify corresponding components. The differences in these systems will be discussed in more detail below.

The impurity detection system of FIG. 2 provides a system for detecting and quantifying gaseous impurities in, for example, an oxygen gas stream under continuous flow conditions.

Because the molecular weight of oxygen is close to the molecular weight of argon, the membrane system 250' located within the exchange column 40 is different than the membrane system 250 utilized in the embodiment of FIG. 1 in which the sample gas source 160 is hydrogen. For analysis of impurities when the sample gas source 160 is oxygen gas, the series of hollow fibers 260 is preferably replaced with a high temperature ceramic membrane 265 that is selectively permeable for oxygen and is potted at both the gas inlet end 210 and the gas outlet end 220. One example of such a high temperature ceramic device useful in this invention is a solid electrolyte ionic or mixed conductor, also known as a "SELIC" device such as described in U.S. Pat. Nos. 5,557,951, 5,837,125 and 5,935,298, the disclosures of which are incorporated herein by reference. An annular space 270 surrounds the high temperature ceramic membrane 265 and is bounded by the inside of hollow tube 200, the gas inlet end 210 and the gas outlet end 220 of hollow tube 200. Utilizing the high temperature ceramic membrane 265 allows selective diffusion of oxygen gas from the permeate stream 300. Alternatively, the membrane system 250' may be replaced with a high capacity oxygen adsorbent to selectively consume the oxygen gas which is then replaced with argon gas.

A disadvantage arising when using the high temperature ceramic membrane 265 is that the system operates at high temperatures, typically from about 800□C to about 1000□C. At such high temperatures, carbon-containing compounds such as methane, higher aliphatic hydrocarbons, and carbon monoxide will likely react with the excess oxygen sample gas and be combusted to generate carbon dioxide. Consequently, it becomes difficult to quantify the concentrations of each impurity individually; instead, a carbon dioxide concentration related to the total amount of combustible carbon compounds can be reported. Reporting the total carbon content in a sample as carbon dioxide may be acceptable to most semiconductor customers.

In this embodiment, the source of the carrier gas 65 is argon, and the source of the sample gas containing impurities 160 is oxygen. A continuous stream of argon gas enters the carrier gas pathway 10 at a rate ranging from about 20 cc/min to about 200 cc/min and a pressure ranging from about 10 psig to about 150 psig, which is regulated by the carrier gas flow control unit 100. The continuous stream of argon gas passes through the getter 70 and reaches the branch point 80 where the argon gas not filling the carrier gas pathway 10 fills the carrier gas purge pathway 20, which supplies a continuous argon stream to the annular space 270 of the exchange column 40 via purified carrier gas inlet port

280. A continuous stream of oxygen sample gas containing impurities enters the sample gas pathway 30. The carrier gas pathway 10 and sample gas pathway 30 intersect at junction 110 thereby causing the argon and oxygen gas streams to combine and form a combined gas feed stream 290. The ratio of oxygen sample gas to the argon carrier gas in the combined gas feed stream 290 ranges from about 4:1 to about 1:4 and preferably from about 2:1 to about 1:2 and more preferably is about 1:1.

The combined gas feed stream 290 enters the exchange column 40 at the feed stream inlet port 230 at a pressure ranging from about 50 psig to about 120 psig. Oxygen gas diffuses from the high temperature ceramic membrane 265 into the annular space 270 as the combined gas feed stream 290 passes through the exchange column 40. The diffused oxygen gas and argon gas combine within the annular space 270 to form a permeate stream 300. If oxygen gas is allowed to build up in the annular space 270, the diffusion rate of the oxygen gas rapidly will decrease. The carrier gas purge pathway 20 supplies purified argon gas in the form of a purge stream 310 to the annular space 270 within the exchange column 40 at a rate of about one 1/min. The purge stream 310 is introduced at atmospheric pressure into the annular space 270 at the purified carrier gas inlet port 280 of exchange column 40. The purge stream 310 sweeps the diffused oxygen gas located within the annular space 270 out of exchange column 40 through permeate stream vent 240. In this fashion, the oxygen gas concentration within the annular space 270 is maintained near zero, thereby maximizing the oxygen gas diffusion rate from the high temperature ceramic membrane 265 into the annular space 270.

Gas flow exiting the exchange column 40 at the retentate stream outlet port 180 is referred to as a retentate stream 320. The retentate stream 320 exits the exchange column 40 and enters the retentate pathway 50 at a flow rate ranging from about 50 cc/min to about 500 cc/min. The retentate pathway 50 communicates with the exchange column 40 and the analyzer 60.

A back-pressure regulator 190 is located within the retentate pathway 50 between retentate stream outlet port 180 and the analyzer 60. The back-pressure regulator 190 functions to maintain proper pressure of the combined gas feed stream 290 as it enters the exchange column 40 and flows through the high temperature ceramic membrane 265. The back-pressure regulator 190 also serves to maintain a constant pressure within the retentate pathway 50 which, in turn, allows constant inlet pressure to the analyzer 60, thereby stabilizing the response of the analyzer 60. The retentate stream 320 contains the impurities of interest originally in the sample oxygen gas now in the argon carrier gas which is suitable for introduction and analysis into the emission spectroscopic analyzer 60.

Figure 3:
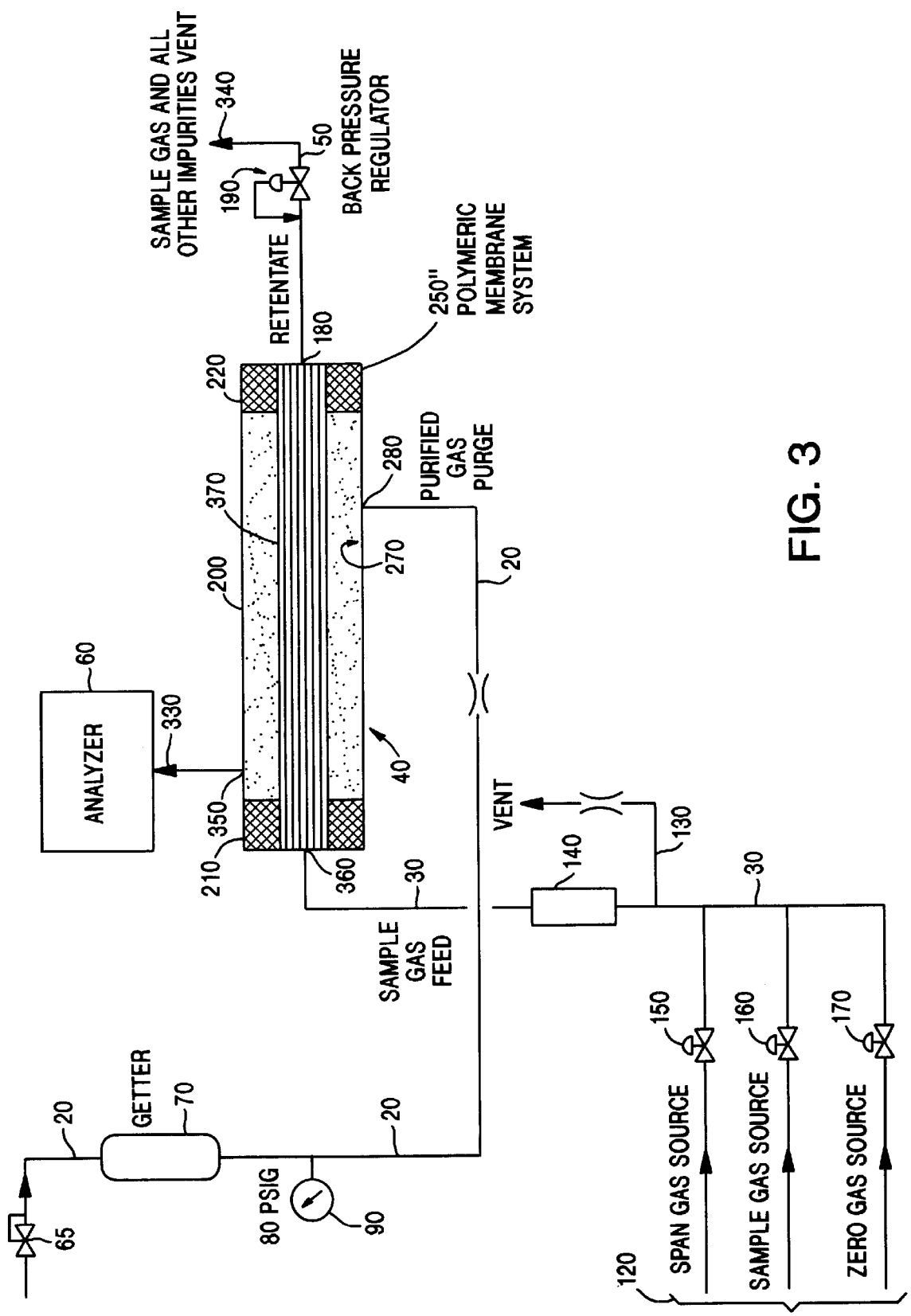
FIG. 3 is a schematic diagram of an impurity detection system of the present invention configured for analysis of a pre-selected gas impurity.

In yet another embodiment, the impurity detection system shown in FIG. 3 is configured such that a single impurity of interest diffuses from a sample gas 160 into a carrier gas 65 in which analysis can be performed. The diffusion of the single impurity of interest is accomplished through use of a membrane system 250" that is selectively permeable for the impurity of interest. The configuration is basically similar to that of FIG. 1 with like reference numerals used to identify corresponding components.

As shown in FIG. 3, the impurity detection system for measuring a single impurity of interest comprises a carrier gas purge pathway 20, a sample gas pathway 30, an exchange column 40, a retentate pathway 50, a permeate pathway 330 and an analyzer 60.

The carrier gas purge pathway 20 comprises a source of carrier gas 65 in communication with a carrier gas getter 70, a carrier gas pressure gauge 90 and the exchange column 40.

The sample gas pathway 30 comprises a valve manifold 120, in communication with a sample gas vent 130, a sample gas flow control unit 140 and the exchange column 40. The valve manifold 120 further comprises a span gas source 150, a sample gas source 160 and a zero gas source 170.

The retentate pathway 50 communicates between a retentate stream outlet port 180 of the exchange column 40 and a retentate pathway vent 340. A back-pressure regulator 190 is located along the retentate pathway 50 between exchange column 40 and the retentate pathway vent 340.

The permeate pathway 330 communicates between a permeate stream outlet port 350 of the exchange column 40 and the analyzer 60. In this embodiment, the analyzer 60 can be an emission spectrometer of the type discussed above with respect to the embodiment shown in FIG. 1.

The exchange column 40 comprises a hollow tube 200 with a gas inlet end 210 and a gas outlet end 220, a sample gas inlet port 360, a purified carrier gas inlet port 280, the retentate stream outlet port 180, a permeate stream outlet port 350 and a membrane system 250".

The membrane system 250" of the exchange column 40 differs depending upon the identity of the impurity of interest, which may include, but is not limited to water, methane, carbon dioxide and oxygen. Generally, the membrane system 250" will be selectively permeable for the impurity of interest. When the impurity of interest is water, for example, the membrane system 250" comprises a selectively permeable membrane 370 which is selectively permeable for water and is potted at both the gas inlet end 210 and the gas outlet end 220 of the exchange column 40. An annular space 270 surrounds the selectively permeable membrane 370 and is bounded by the inside of hollow tube 200, the gas inlet end 210 and the gas outlet end 220 of hollow tube 200.

In one embodiment, the source of the carrier gas 65 is argon, the source of sample gas 160 is nitrogen and the impurity of interest is water. A continuous stream of argon gas enters the carrier gas pathway 10 at a rate ranging from about 50 cc/min to about 500 cc/min and a pressure ranging from about 10 psig to about 150 psig. The continuous stream of argon gas passes through the getter 70 and enters the annular space 270 of the exchange column 40 via the purified carrier gas inlet port 280. A continuous stream of nitrogen gas containing water enters the sample gas pathway 30 at a rate ranging from about 50 cc/min to about 200 cc/min and a pressure ranging from about 10 psig to about 150 psig, which is regulated by the sample gas flow control unit 140. The continuous stream of nitrogen enters the exchange column 40 via the sample gas inlet port 360.

Once inside the exchange column 40, water passes through the membrane system 250 into the annular space 270 where the water mixes with the carrier gas argon to form a permeate stream 300. The permeate stream 300 exits the exchange column 40 via the permeate stream outlet port 350 and enters the permeate pathway 330 which flows into the analyzer 60 for analysis at a rate ranging from about 50 cc/min to about 500 cc/min.

The nitrogen sample gas, with the water removed, exits the exchange column 40 through the retentate stream outlet port 180 and enters the retentate pathway 50 where it is vented to the outside environment via the retentate pathway vent 340 at a pressure ranging from about 10 psig to about 150 psig.

Calibration of the analyzer 60 is accomplished by supplying the zero gas source 120, which is the sample gas with all impurities removed, and the span gas source 150 to the exchange column 40. Adjustments may be made in the analyzer 60 for any sample gas which diffuses into the permeate stream 300 and affects the baseline of the analyzer 60; similarly, adjustments may be made to compensate for less than 100% transfer of water into the permeate stream 300.

While the present invention is described above with respect to what is currently considered to be its preferred embodiments, it is to be understood that the invention is not limited to that described above. To the contrary, the invention is intended to cover various modifications and equivalent arrangements included within the spirit and scope of the appended claims.

I claim:

1. A method of analyzing a sample gas for the presence of at least one gas impurity in the sample gas, the method comprising the steps of:
    (a) combining a stream of a sample gas with a stream of a carrier gas to generate a combined stream of gas;
    (b) directing the combined stream of gas through a column which preferentially removes the sample gas from the combined stream to produce a retentate stream of gas; and
    (c) analyzing the retentate stream of gas by emission spectroscopy for the presence of at least one gas impurity.

2. A method according to claim 1, wherein the column comprises a semipermeable membrane which is preferentially permeable to the sample gas.

3. A method according to claim 2, wherein the semipermeable membrane is made of a material selected from the group consisting of polysulfone, ceramic and palladium.

4. A method according to claim 3, wherein the semipermeable membrane is made of polysulfone.

5. A method according to claim 3, wherein the semipermeable membrane is made of ceramic.

6. A method according to claim 3, wherein the semipermeable membrane is made of palladium.

7. A method according to claim 1, wherein the sample gas is selected from the group consisting of hydrogen and oxygen.

8. A method according to claim 1, wherein the sample gas is hydrogen.

9. A method according to claim 1, wherein the sample gas is oxygen.

10. A method according to claim 1, wherein the carrier gas is selected from the group consisting of argon, helium and nitrogen.

11. A method according to claim 1, wherein the carrier gas is argon.

12. A method according to claim 1, wherein the carrier gas is helium.

13. A method according to claim 1, wherein the carrier gas is nitrogen.

14. A method according to claim 1, wherein the ratio of the sample gas to the carrier gas in the combined gas stream is from about 4:1 to about 1:4.

15. A method according to claim 14, wherein the ratio of the sample gas to the carrier gas in the combined gas stream is from about 2:1 to about 1:2.

16. A method according to claim 14, wherein the ratio of the sample gas to the carrier gas in the combined gas stream is about 1:1.

17. A method according to claim 1, wherein the at least one gas impurity is selected from the group consisting of nitrogen, methane, water, carbon monoxide, carbon dioxide and oxygen.

18. A method of analyzing a sample gas for the presence of at least one gas impurity in the sample gas, the method comprising the steps of:
    (a) directing a stream of carrier gas through a column;
    (b) directing a stream of sample gas to the column which allows selective permeation of the at least one gas impurity from the stream of sample gas into the stream of carrier gas to produce a permeate stream of gas; and
    (c) analyzing the permeate stream of gas by emission spectroscopy for the presence of the at least one gas impurity.

19. A method according to claim 18, wherein the column comprises a selectively permeable membrane which is preferentially permeable to the at least one gas impurity.

20. A method according to claim 19, wherein the selectively permeable membrane is made of a material selected from the group consisting of polysulfone, ceramic and palladium.

21. A method according to claim 18, wherein the sample gas is selected from the group consisting of hydrogen, oxygen, nitrogen and air.

22. A method according to claim 18, wherein the sample gas is nitrogen.

23. A method according to claim 18, wherein the carrier gas is selected from the group consisting of argon, helium and nitrogen.

24. A method according to claim 18, wherein the carrier gas is argon.

25. A method according to claim 18, wherein the carrier gas is helium.

26. A method according to claim 18, wherein the carrier gas is nitrogen.

27. A method according to claim 18, wherein the at least one gas impurity is selected from the group consisting of methane, water, nitrogen, carbon monoxide, carbon dioxide and oxygen.

* * * * *